(12) United States Patent
Zhang et al.

(10) Patent No.: US 11,927,489 B2
(45) Date of Patent: Mar. 12, 2024

(54) PREHEATED THERMOMETER

(71) Applicant: INSTITUTE OF FLEXIBLE ELECTRONICS TECHNOLOGY OF THU, ZHEJIANG, Zhejiang (CN)

(72) Inventors: Yan Zhang, Zhejiang (CN); Honghong Su, Zhejiang (CN)

(73) Assignee: INSTITUTE OF FLEXIBLE ELECTRONICS TECHNOLOGY OF THU, ZHEJIANG, Jiaxing (CN)

( * ) Notice: Subject to any disclaimer, the term of this patent is extended or adjusted under 35 U.S.C. 154(b) by 503 days.

(21) Appl. No.: 17/037,615

(22) Filed: Sep. 29, 2020

(65) Prior Publication Data

US 2021/0010875 A1    Jan. 14, 2021

Related U.S. Application Data

(63) Continuation of application No. PCT/CN2018/118105, filed on Nov. 29, 2018.

(30) Foreign Application Priority Data

Oct. 25, 2018 (CN) .......................... 201821741349.0

(51) Int. Cl.
  *G01K 13/20* (2021.01)
  *G01K 1/00* (2006.01)
(52) U.S. Cl.
  CPC ............... *G01K 13/20* (2021.01); *G01K 1/00* (2013.01)
(58) Field of Classification Search
  CPC .......... G01K 1/00; G01K 13/20; G01K 13/25; G01K 1/08; G01K 1/14; G01K 1/16; G01K 1/18; G01K 13/10; G01K 1/43; A61B 5/01; A61B 2562/0271; A61B 2562/12; A61B 2562/16; A61B 2562/164; A61B 5/259; A61B 2560/0412; A61B 5/6833; A61B 5/6898; G01N 27/403
  See application file for complete search history.

(56) References Cited

U.S. PATENT DOCUMENTS 4,991,976 A * 2/1991 Byles ...................... G01K 1/18
  374/138
9,943,232 B2 * 4/2018 Kroetz ..................... G01K 1/18
  (Continued)

FOREIGN PATENT DOCUMENTS

CN         1880928      12/2006
CN         104068831    10/2014
            (Continued)

OTHER PUBLICATIONS

WIPO, ISR for PCT/CN2018/118105, Jul. 31, 2019.

*Primary Examiner* — Daniel R Miller
*Assistant Examiner* — Eric Sebastian Von Wald
(74) *Attorney, Agent, or Firm* — Hodgson Russ LLP

(57) ABSTRACT

Provided is a preheating thermometer, including a temperature measuring assembly, and a preheating assembly disposed on the temperature measuring assembly. The preheating assembly includes a heating material layer and a sealing film covering the heating material layer to isolate the heating material layer from air. When the preheating thermometer is used for body temperature measurement, the sealing film is removed to allow the heating material layer to produce heat due to the contact of the heating material layer with the air.

12 Claims, 3 Drawing Sheets

(56) References Cited

U.S. PATENT DOCUMENTS

| | | | | |
|---|---|---|---|---|
| 2008/0273573 A1* | 11/2008 | Gerder | ................. | G01K 1/16 |
| | | | | 374/E7.042 |
| 2018/0256100 A1* | 9/2018 | Li | ................. | A61B 5/6816 |
| 2019/0175096 A1* | 6/2019 | Xi | ................. | A61F 13/00051 |

FOREIGN PATENT DOCUMENTS

| | | | | | |
|---|---|---|---|---|---|
| CN | 105120809 | | 12/2015 | | |
| CN | 106932119 | A * | 7/2017 | | |
| EP | 1249691 | | 10/2002 | | |
| EP | 1249691 | A1 * | 10/2002 | ............... | G01K 1/16 |
| FR | 2850754 | A1 * | 8/2004 | ............... | G01K 1/16 |
| JP | 4354459 | B2 * | 10/2009 | .......... | B01L 3/50851 |
| JP | 2017077396 | A * | 4/2017 | | |
| RU | 2367541 | C1 * | 9/2009 | | |
| TW | 337347 | | 7/1998 | | |
| WO | WO-2017140525 | A1 * | 8/2017 | | |

* cited by examiner

PREHEATED THERMOMETER

CROSS-REFERENCE TO RELATED APPLICATIONS

This application is a continuation of International Application No. PCT/CN2018/118105, filed Nov. 29, 2018, which claims priority to Chinese Patent Application Serial No. 201821741349.0, filed Oct. 25, 2018, the entire disclosures of which are incorporated herein by reference.

FIELD

The present disclosure relates to a field of thermometer technology, in particularly to a preheating thermometer.

BACKGROUND

With development of wearable device technology, application of wearable devices in the medical field has drawn attention from technicians, and wearable flexible thermometers have been studied.

A conventional method of measuring body temperature in an armpit of a user is performed as follows. A thermometer (such as a mercury thermometer, an electronic thermometer and a wearable thermometer) is placed in the armpit of the user, the user clamps the thermometer and waits for a period of time. Then, the thermometer is taken out to read body temperature data. Due to the limited self-heating ability of the human armpit, when the thermometer is placed in the armpit, temperatures of the thermometer and skin surrounding the thermometer usually has a large difference from the armpit temperature to be measured. As a result, it needs a long time to heat the thermometer to be close to a normal axillary temperature. Usually, it needs more than 10 min to measure the body temperature, and it may take a longer time when it is in winter. Therefore, the existing manner for axillary temperature measurement needs a long measuring time and a low measuring efficiency, and cannot meet requirements of comfortable wearing and continuous temperature measurement.

SUMMARY

The present disclosure provides in embodiments a preheating thermometer, including a temperature measuring assembly, and a preheating assembly disposed on the temperature measuring assembly. The preheating assembly includes a heating material layer and a sealing film covering the heating material layer.

In an embodiment of the present disclosure, the preheating assembly further includes a heating material container, the heating material layer is fixed in the heating material container, and the sealing film covers the heating material container.

In an embodiment of the present disclosure, a wall of the heating material container is made of a gas-permeable film with a plurality of holes for ventilation.

In an embodiment of the present disclosure, the heating material container has an opening to allow the heating material layer to be in contact with air through the opening, and the sealing film covers the opening.

In an embodiment of the present disclosure, the preheating assembly includes a plurality of the sealing films, a surface of the heating material container is divided into a plurality of regions, and each of the sealing films covers one of the regions.

In an embodiment of the present disclosure, the preheating assembly further includes a temperature detection device.

In an embodiment of the present disclosure, the sealing film is used to form a sealing cover, and the temperature measuring assembly and the preheating assembly are both sealed by the sealing cover.

In an embodiment of the present disclosure, the temperature measuring assembly includes a substrate and a temperature sensor arranged on the substrate.

In an embodiment of the present disclosure, the substrate is a flexible substrate, and the temperature sensor is a flexible temperature sensor.

In an embodiment of the present disclosure, the preheating assembly is fixed to the substrate by a second adhesive layer, and the preheating assembly and the temperature sensor are respectively located on different surfaces of the substrate, or are located on the same surface of the substrate.

In an embodiment of the present disclosure, the heating material container and the substrate are formed in one, and the preheating assembly and the temperature sensor are respectively located on different surfaces of the substrate, or are located on the same surface of the substrate.

In an embodiment of the present disclosure, a temperature increment of the temperature measuring assembly is controlled by an amount of the heating material layer.

DETAILED DESCRIPTION

In order to further illustrate technical means and effects adopted by the present disclosure to achieve the intended purpose of the present disclosure, embodiments of the present disclosure will be described in detail in the following descriptions with reference to the accompanying drawings.

The present disclosure provides a preheating thermometer, which is capable of quickly raising a temperature of the thermometer to a target temperature. In this case, the time period for the flexible thermometer to measure human body temperature is greatly shortened, thus facilitating examination and diagnosis performed by a doctor.

Figure 1:
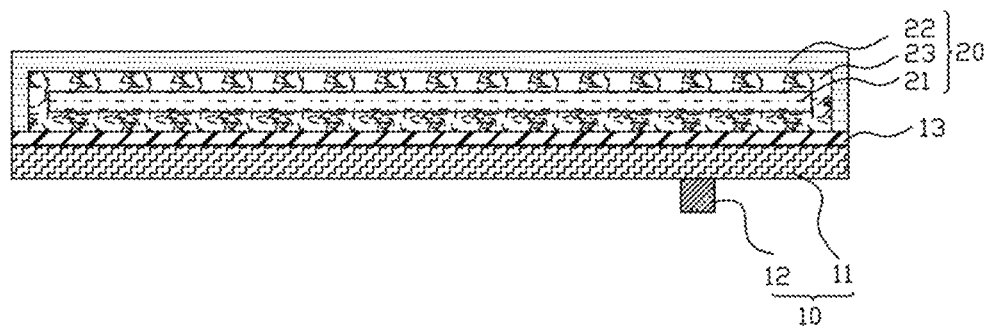
FIG. 1 is a cross-sectional view of a preheating thermometer according to a first embodiment of the present disclosure.
Figure 2:
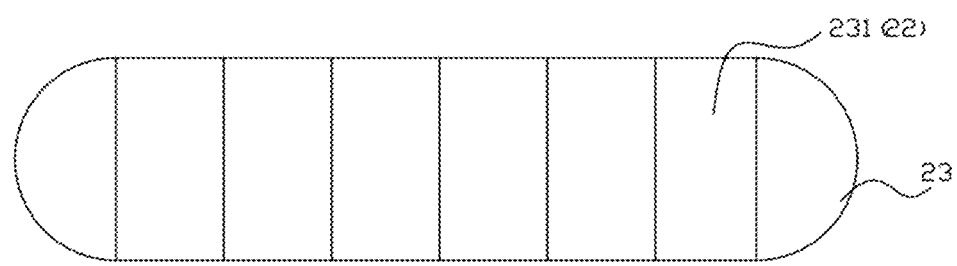
FIG. 2 is a top view of the preheating thermometer of FIG. 1.

FIG. 1 is a cross-sectional view of a preheating thermometer according to a first embodiment of the present disclosure. FIG. 2 is a top view of the preheating thermometer of FIG. 1. As shown in FIGS. 1 and 2, in the first embodiment of the present disclosure, a preheating thermometer includes a temperature measuring assembly 10 and a preheating assembly 20 disposed on the temperature measuring assembly 10. The preheating assembly 20 includes a heating material layer 21 and a sealing film 22 covering the heating material layer 21 to isolate the heating material layer 21 from the air.

When the preheating thermometer provided in this embodiment of the present disclosure is applied for body temperature measurement, the sealing film 22 is removed first, so that the air contacts the heating material layer 21 to allow the heating material layer 21 to produce heat due to the contact of the heating material layer 21 with the air. The heat is transferred to the temperature measuring assembly 10, thus preheating the temperature measuring assembly 10. In this way, the temperature of the temperature measuring assembly 10 may rise quickly at the beginning of the temperature measurement, thus saving time. In other words, the temperature of the preheating thermometer can be quickly increased to the target temperature, so that the time period for the flexible thermometer to measure human body temperature is greatly shortened, thus facilitating examination and diagnosis performed by a doctor.

Figure 7:
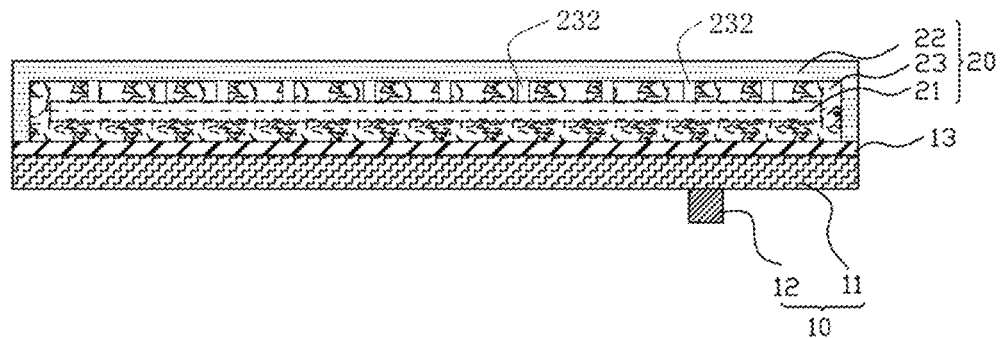
FIG. 7 is a cross-sectional view of a preheating thermometer according to a fifth embodiment of the present disclosure.

Further, in order to facilitate the fixing of the heating material layer 21, the preheating assembly 20 further includes a heating material container 23, the heating material layer 21 is fixed in the heating material container 23, and the sealing film 22 covers the heating material container 23. In this embodiment, in order to facilitate the contact of the heat generating material 21 with the air, a wall of the heating material container 23 is made of a gas-permeable film with a plurality of holes 232 for ventilation (as shown in FIG. 7). For example, the hole 232 has a size of a few microns to tens of millimeters.

Figure 9:
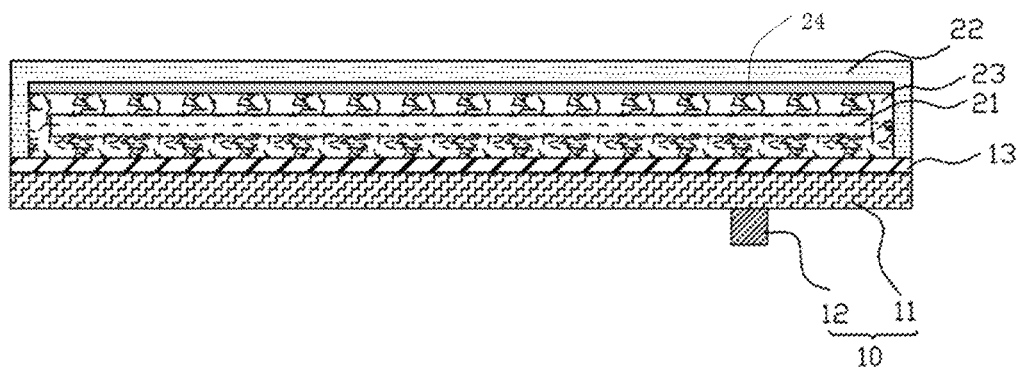
FIG. 9 is a cross-sectional view of a preheating thermometer according to a seventh embodiment of the present disclosure.

In this embodiment, the sealing film 22 may be attached and covered on a surface of the heating material container 23 by a first adhesive layer 24 (as shown in FIG. 9) to prevent the heating material layer 21 from being in contact with the air. When the preheating thermometer is applied, the sealing film 22 is peeled off to allow the heating material layer to be in contact with the air and thus produce heat.

In other embodiments of the present disclosure, the sealing film 22 may be used to form a sealing cover, and the temperature measuring assembly 10 and the preheating assembly 20 are both sealed by the sealing cover. When the temperature measuring assembly 10 and the preheating assembly 20 are taken out of the sealing cover, the heating material layer may be reacted with the air to generate heat.

Figure 8:
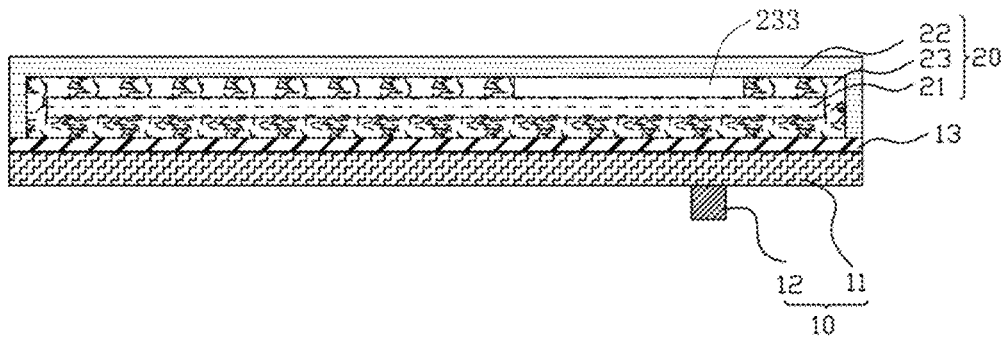
FIG. 8 is a cross-sectional view of a preheating thermometer according to a sixth embodiment of the present disclosure.

It should be understood that in some other embodiments of the present disclosure, the wall of the heating material container 23 may not be made of the gas-permeable film. In this case, the heating material container 23 has an opening 233 (as shown in FIG. 8) to allow the heating material layer 21 to be in contact with the air through the opening 233, and the sealing film 22 covers the opening 233.

Further, as shown in FIG. 2, the preheating assembly 20 includes a plurality of the sealing films 22, a surface of the heating material container 23 is divided into a plurality of regions 231, and each of the sealing films 22 covers one of the regions 231. When the preheating thermometer is applied, the sealing film 22 in one region, several regions or all regions can be peeled off according to operating environment, operator or other factors, so as to increase the number of application scenarios of the preheating thermometer of the present disclosure.

A material for the heating material layer 21 may include iron powder, activated carbon, vermiculite and an inorganic salt (such as sodium chloride, potassium chloride and any water-soluble non-heavy metal salt). Specifically, a particle of an iron powder heating material layer 21 may have a particle size of several microns to several tens of microns.

For example, a preheating mechanism of the iron powder may be as follows.

At negative electrode: $2Fe-4e^-=2Fe^{2+}+heat$; 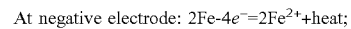

At positive electrode: $O_2+2H_2O+4e^-=4OH^-$; 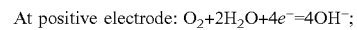

Overall reactions: $2Fe+O_2+2H_2O=2Fe(OH)_2+heat$; 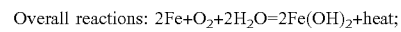

$2Fe(OH)_2+H_2O+½O_2=2Fe(OH)_3+heat$; 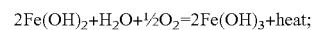

$2Fe(OH)_3=Fe_2O_3+3H_2O$. 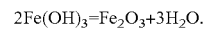

On this basis, the iron powder has a specific heat quantity indicated by q in KJ/mol, and a specific heat capacity indicated by C in KJ/(kg·° C.), the iron powder has a specific mass indicated as $m_1$ and the temperature measuring assembly 10 has a specific mass indicated as $m_2$, such that a temperature change Δt can be controlled in a range of 5 to 15° C. and calculated according the following formula.

$$\Delta t=q \cdot m_1/(56 \cdot C \cdot m_2)$$

In this case, the iron powder is reacted with oxygen and moisture in the air passing through the gas-permeable film to obtain iron oxides and release heat. NaCl may be used to corrode the iron powder and accelerate oxidation rate of the iron powder. Vermiculite has a porous structure and thus may be used as a carrier, such that there is enough space for the iron powder to react with oxygen and heat preservation may be realized. In other embodiments of the present disclosure, vermiculite may be replaced by wood flour having a same function. Due to the structure of vermiculite, vermiculite may have a better effect compared with the wood flour, which will be more helpful to improve heating time period and reaction rate to at least some extent. The activated carbon has a function of absorbing excess water generated during the reaction process to ensure the reaction environment. By controlling amount of each substance, it can be ensured that the temperature of the temperature measuring assembly 10 is lower than the normal temperature of the human body.

Further, the preheating assembly 20 includes a temperature detection device (not shown). Therefore, the temperature of the preheating assembly 20 can be controlled below the normal temperature of the human body, avoiding interference to the temperature measurement of the preheating thermometer.

Further, a temperature increment of the temperature measuring assembly 10 is controlled by an amount of the heating material layer. For example, the temperature increment of 5 to 15° C. of the temperature measuring assembly 10 may be controlled by the amount of the heating material layer.

In addition, as shown in FIG. 1, in this embodiment, the preheating assembly 20 is fixed to the temperature measuring assembly 10 by a second adhesive layer 13. The temperature measuring assembly 10 includes a substrate 11 and a temperature sensor 12 arranged on the substrate 11. In this embodiment, both the substrate 11 and the temperature sensor 12 have flexibility, that is, the substrate 11 is a flexible substrate and the temperature sensor is a flexible temperature sensor, to make the thermometer fit the human skin more closely.

In this embodiment, in order to reduce the influence of the preheating assembly 20 on the human skin, the preheating assembly 20 and the temperature sensor 12 are respectively located on different surfaces of the substrate 11.

In this embodiment, by arranging the preheating assembly 20 in the present preheating thermometer, the preheating assembly 20 can be used to heat the thermometer during the application of the thermometer, to allow the thermometer to reach a target temperature quickly, such that the time period for the flexible thermometer to measure human body temperature is greatly shortened, thus facilitating examination and diagnosis performed by a doctor.

Figure 3:
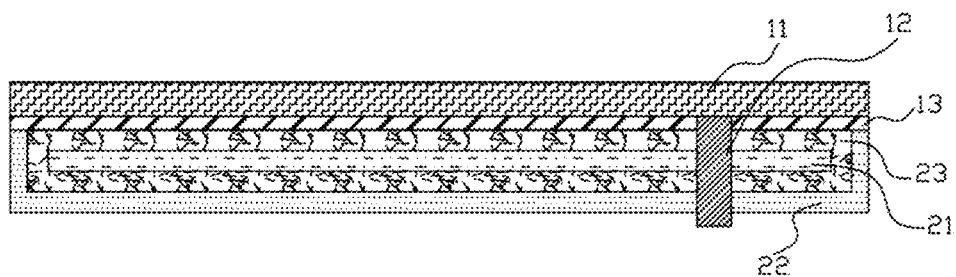
FIG. 3 is a cross-sectional view of a preheating thermometer according to a second embodiment of the present disclosure.
Figure 4:
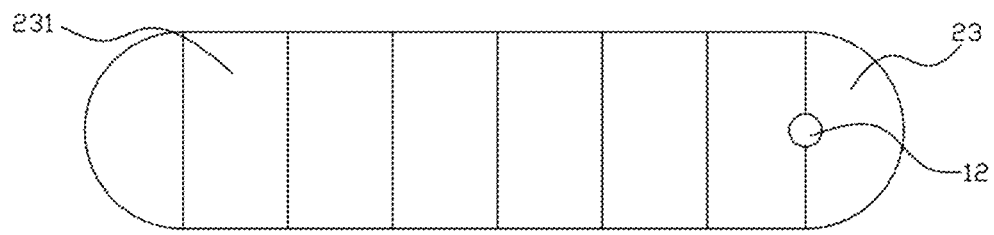
FIG. 4 is a bottom view of the preheating thermometer of FIG. 3.

FIG. 3 is a cross-sectional view of a preheating thermometer according to a second embodiment of the present disclosure. FIG. 4 is a bottom view of the preheating thermometer of FIG. 3. As shown in FIGS. 3 and 4, the structure of the preheating thermometer provided by the second embodiment of the present application is substantially the same as that of the first embodiment of the present disclosure, except that in the second embodiment, in order to further accelerate the process of heating the thermometer to the target temperature, the preheating assembly 20 and the temperature sensor 12 are located on the same surface of the substrate 11. Therefore, the heat generated by the preheating assembly 20 can transmit to the temperature sensor 12 more quickly.

Figure 5:
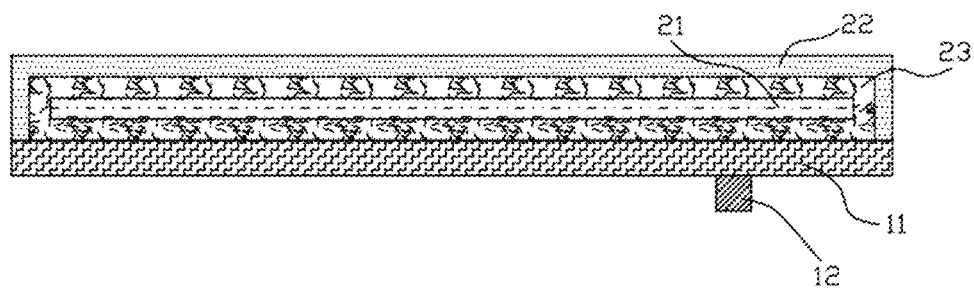
FIG. 5 is a cross-sectional view of a preheating thermometer according to a third embodiment of the present disclosure.

FIG. 5 is a cross-sectional view of a preheating thermometer according to a third embodiment of the present disclosure. The structure of the preheating thermometer provided by the third embodiment of the present application is substantially the same as that of the first embodiment of the present disclosure, except that in the third embodiment, the heating material container 23 is integrally formed on a surface of the substrate 11 away from the temperature sensor 12. In this way, the second adhesive layer 13 can be omitted so as to save production cost and operations on one hand and to transmit the heat on the other hand.

Figure 6:
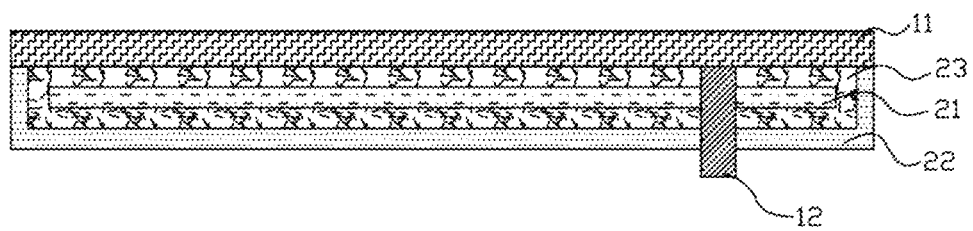
FIG. 6 is a cross-sectional view of a preheating thermometer according to a fourth embodiment of the present disclosure.

FIG. 6 is a cross-sectional view of a preheating thermometer according to a fourth embodiment of the present disclosure. The structure of the preheating thermometer provided by the fourth embodiment of the present application is substantially the same as that of the third embodiment of the present disclosure, except that in the fourth embodiment, the heating material container 23 is integrally formed on a same surface, where the temperature sensor 12 is formed, of the substrate 11.

From the above, by arranging the preheating assembly 20 in the present preheating thermometer, the preheating assembly 20 can be used to heat the thermometer during the application of the thermometer, to allow the thermometer to reach a target temperature quickly, such that the time period for the flexible thermometer to measure human body temperature is greatly shortened, thus facilitating examination and diagnosis performed by a doctor.

It should be noted that above embodiments of the present disclosure are explanatory, and shall not be construed to limit the present disclosure. Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

INDUSTRIAL APPLICABILITY

By arranging the preheating assembly in the present preheating thermometer, the preheating assembly can be used to heat the thermometer during the application of the thermometer, to allow the thermometer to reach a target temperature quickly, such that the time period for the flexible thermometer to measure human body temperature is greatly shortened, thus facilitating examination and diagnosis performed by a doctor.

What is claimed is:

1. A preheating thermometer, comprising:
    a temperature measuring assembly comprising a substrate and a temperature sensor arranged on the substrate, and
    a preheating assembly disposed on the substrate of the temperature measuring assembly, wherein the preheating assembly comprises a heating material layer and a sealing film covering the heating material layer to isolate the heating material layer from air, wherein when the preheating thermometer is used for body temperature measurement, the sealing film is removable to allow the heating material layer to produce heat due to the contact of the heating material layer with the air,
    wherein the substrate is in a form of a layer, the preheating assembly and the temperature sensor are respectively located on different surfaces of the substrate, and the temperature sensor, the substrate, the heating material layer and the sealing film are stacked.

2. The preheating thermometer according to claim 1, wherein the preheating assembly further comprises a heating material container, the heating material layer is fixed in the heating material container, and the sealing film covers the heating material container.

3. The preheating thermometer according to claim 2, wherein a wall of the heating material container is made of a gas-permeable film with a plurality of holes for ventilation.

4. The preheating thermometer according to claim 2, wherein the heating material container has an opening to allow the heating material layer to be in contact with air through the opening, and the sealing film covers the opening.

5. The preheating thermometer according to claim 2, wherein the preheating assembly comprises a plurality of the sealing films, a surface of the heating material container is divided into a plurality of regions, and one of the sealing films has a same shape as one of the regions and covers the one of the regions.

6. The preheating thermometer according to claim 1, wherein the substrate is a flexible substrate, and the temperature sensor is a flexible temperature sensor.

7. The preheating thermometer according to claim 1, wherein the preheating assembly is fixed to the substrate by an adhesive layer.

8. The preheating thermometer according to claim 1, wherein the heating material container and the substrate are integrally formed.

9. The preheating thermometer according to claim 1, wherein the preheating assembly further comprises a temperature detection device configured to control a temperature of the preheating assembly below a normal temperature of a human body.

10. The preheating thermometer according to claim 1, wherein the sealing film is used to form a sealing cover, and the temperature measuring assembly and the preheating assembly are both sealed by the sealing cover.

11. The preheated thermometer according to claim 1, wherein a specific temperature increment of the temperature measuring assembly is controlled by a specific quantity of the heating material layer.

12. The preheating thermometer according to claim 1, wherein a material for the heating material layer comprises iron powder, activated carbon, vermiculite and an inorganic salt.

* * * * *